United States Patent [19]

Christoudias

[11] Patent Number: 5,100,421
[45] Date of Patent: Mar. 31, 1992

[54] CHRISTOUDIAS CURVED NEEDLE SUTURE ASSEMBLY

[75] Inventor: George C. Christoudias, New Milford, N.J.

[73] Assignee: Cyprus Endosurgical Tools, Inc., Saddle River, N.J.

[21] Appl. No.: 650,778

[22] Filed: Feb. 5, 1991

[51] Int. Cl.$^5$ .............................................. A61B 17/00
[52] U.S. Cl. .................................................... 606/147
[58] Field of Search ................ 606/139, 144, 145, 147

[56] References Cited

U.S. PATENT DOCUMENTS

| | | | |
|---|---|---|---|
| 3,168,097 | 2/1965 | Dormia | 606/147 |
| 3,417,752 | 12/1968 | Butler | 606/147 |
| 4,635,638 | 1/1987 | Weintraub et al. | 606/147 |
| 5,037,433 | 8/1991 | Wilk et al. | 606/139 |

Primary Examiner—Stephen C. Pellegrino
Assistant Examiner—Gary Jackson
Attorney, Agent, or Firm—Richard A. Joel

[57] ABSTRACT

An assembly to facilitate endoscopic surgery comprises an endoscopic dual head needle holder, a needle transporter, a needle guide forceps and an endoscopic suture with a terminal loop. The assembly is utilized in a unique process wherein the tissue to be sutured is grasped by the needle guide forceps and the needle inserted into and through the tissue with the assembly. The needle is inserted into a body cavity with a transporter, a first needle holder is advanced to the appropriate level and the needle transferred to the first needle holder. The needle is then passed through the tissue to a second needle holder and then back to the first needle holder. The needle is then passed through the suture loop securing the thread on the tissues. Continuous suturing is then achieved by successive passage of the needle by the first needle holder through the tissues by the first needle holder, retrieval of the needle by the second needle holder and passage of it back to the first needle holder. Continuous suturing is therefore accomplished at a fast, safe and effective pace. Finally, the needle is transferred to a transport instrument, the thread cut and the needle removed from the cavity by the transporter.

10 Claims, 3 Drawing Sheets

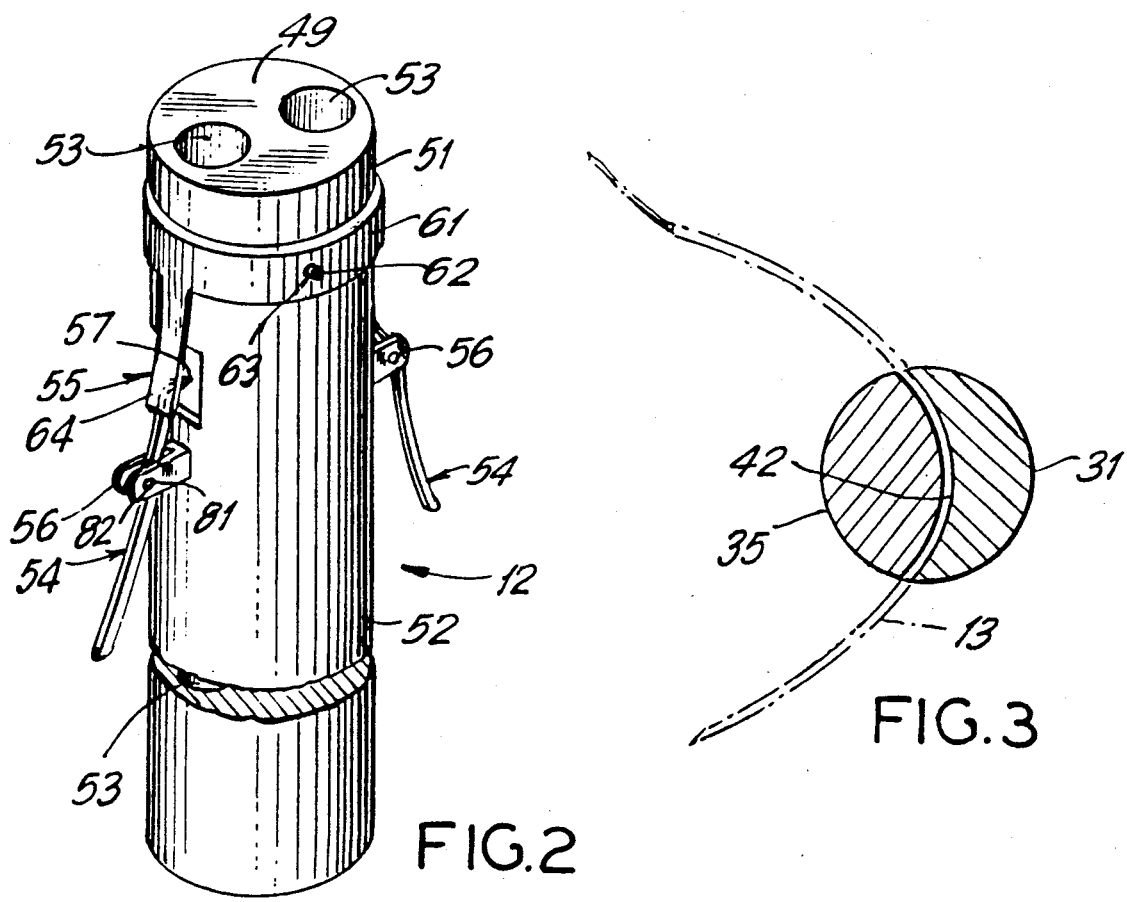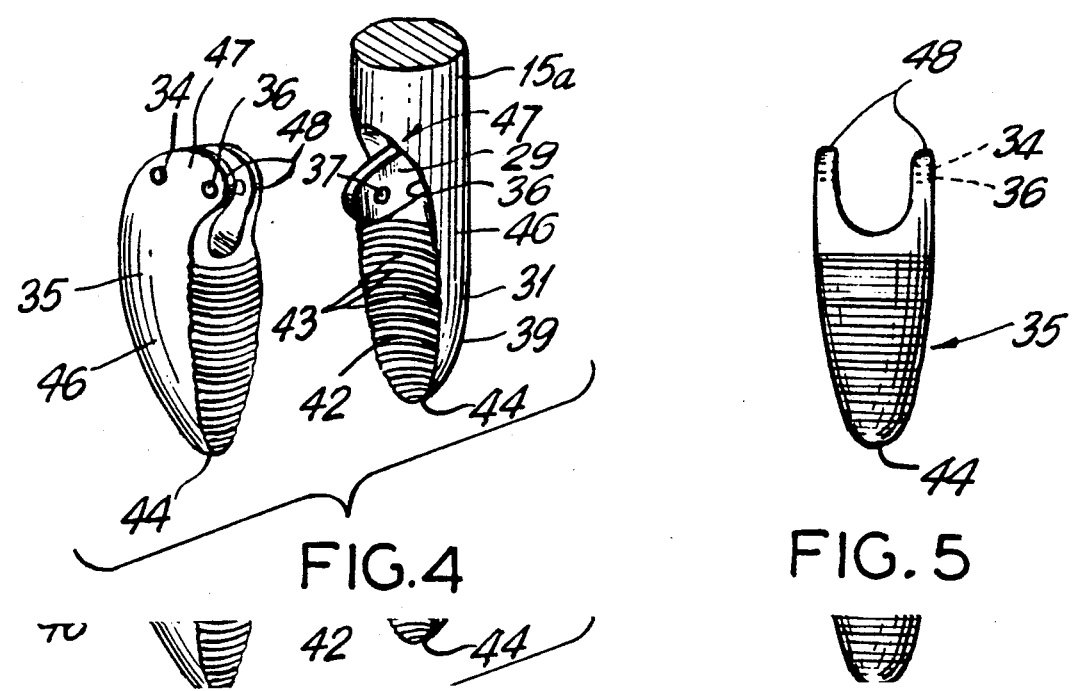

CHRISTOUDIAS CURVED NEEDLE SUTURE ASSEMBLY

BACKGROUND OF THE INVENTION

"The future for Laparoscopic Surgery is as bright as the light source we rely on to visualize the field, and the only limiting factor is the imagination of surgical practitioners". J. M. Sackier, M.D., G. Berci M.D., *Contemporary Surgery*. Oct. 90 Vol. 37 No. 4.

With endoscopic surgery gaining widespread acceptance in the gynecological and other surgical fields, more and more procedures that were performed with conventional large, painful and temporarily disabling incisions are now utilizing the revolutionary laparoscopic modality. The need for new instruments to perform these procedures is great and the lack of such instruments is a limiting factor in the changeover to endoscopic surgical procedures.

The present invention discloses a basic assembly to facilitate endoscopic surgery. The invention called the "Christoudias Curved Needle Suture Assembly" proposes an endoscopic dual head needle holder which is used with a needle transporter, a needle guide forceps and an endoscopic suture with a terminal loop. The new instrument assembly is nowhere disclosed in the known prior art. Indeed, the prior art, because of the conventional surgical procedures, had little or no use for an instrument assembly which is a key building block in an entirely new and revolutionary surgical technique.

SUMMARY OF THE INVENTION

The present invention comprises a method and assembly for performing endoscopic surgery. The assembly comprises a dual head curved needle holder wherein two needle grasping and holding members are mounted within a support cylinder. The members each include a control end with finger loops, an elongated body and needle grasping jaws at the other end to pass a curved needle back and forth for suturing. The tissue to be sutured is grasped by needle guide tissue forceps and the needle inserted back and forth through the tissue by the holder. When suturing has been completed, the needle is transferred to the needle transport instrument, the thread cut close to the needle and the needle removed from the body cavity by the transporter. An instrument tie of the remaining thread secured the suture line.

Accordingly, an object of this invention is to provide a new and improved method and assembly for endoscopic surgery.

Another object of this invention is to provide a unique dual needle holder assembly to facilitate endoscopic suturing.

A further object of this invention is to provide a unique needle transporter for use with the needle holder assembly to transfer needles to the holder.

A still further object of this invention is to provide a new and improved needle and suturing thread with a terminal loop for use with the novel assembly herein.

A more specific object of this invention is to provide a new and improved method and apparatus for endoscopic surgery which includes means to endoscopically suture tissue utilizing a dual needle holder assembly with means to pass a needle through the tissue after said needle has been transported to the suturing location within a body cavity, a unique needle and suturing thread and means to introduce and remove the needle from the cavity.

DESCRIPTION OF THE DRAWINGS

The above and other objects of the invention may be more clearly seen when viewed in conjunction with the accompanying drawings wherein:

FIG. 2 is a perspective view of the dual head cylinder of the needle holder assembly;

FIG. 3 is a cross-sectional view of the needle holder jaws taken along the line 3—3 of FIG. 1 with a needle shown in phantom;

FIG. 4 is an enlarged perspective view of the jaws shown in FIG. 4;

FIG. 5 is an enlarged plan view of a portion of the movable jaw;

DETAILED DESCRIPTION OF THE INVENTION

Figure 11:
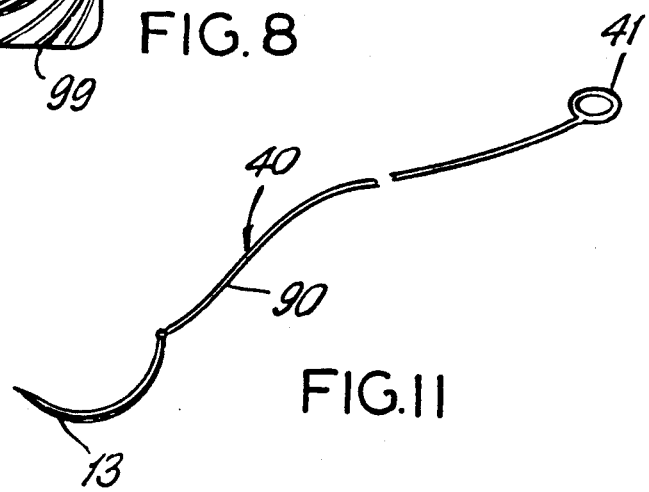
FIG. 11 is a perspective view of a curved needle and suture thread with a terminal loop.

Referring now to the drawings, the invention comprises an endoscopic suture assembly comprised of four main components. The assembly includes a dual head curved needle holder 10 shown in FIG. 1, a needle transporter 20 (FIG. 6), a needle guide tissue forceps 30 (FIG. 9) and an endoscopic suture 40 with a terminal loop 41 (FIG. 11). This invention is a basic tool in a revolutionary new procedure which eliminates the pain and disability of former surgical methods.

Figure 1:
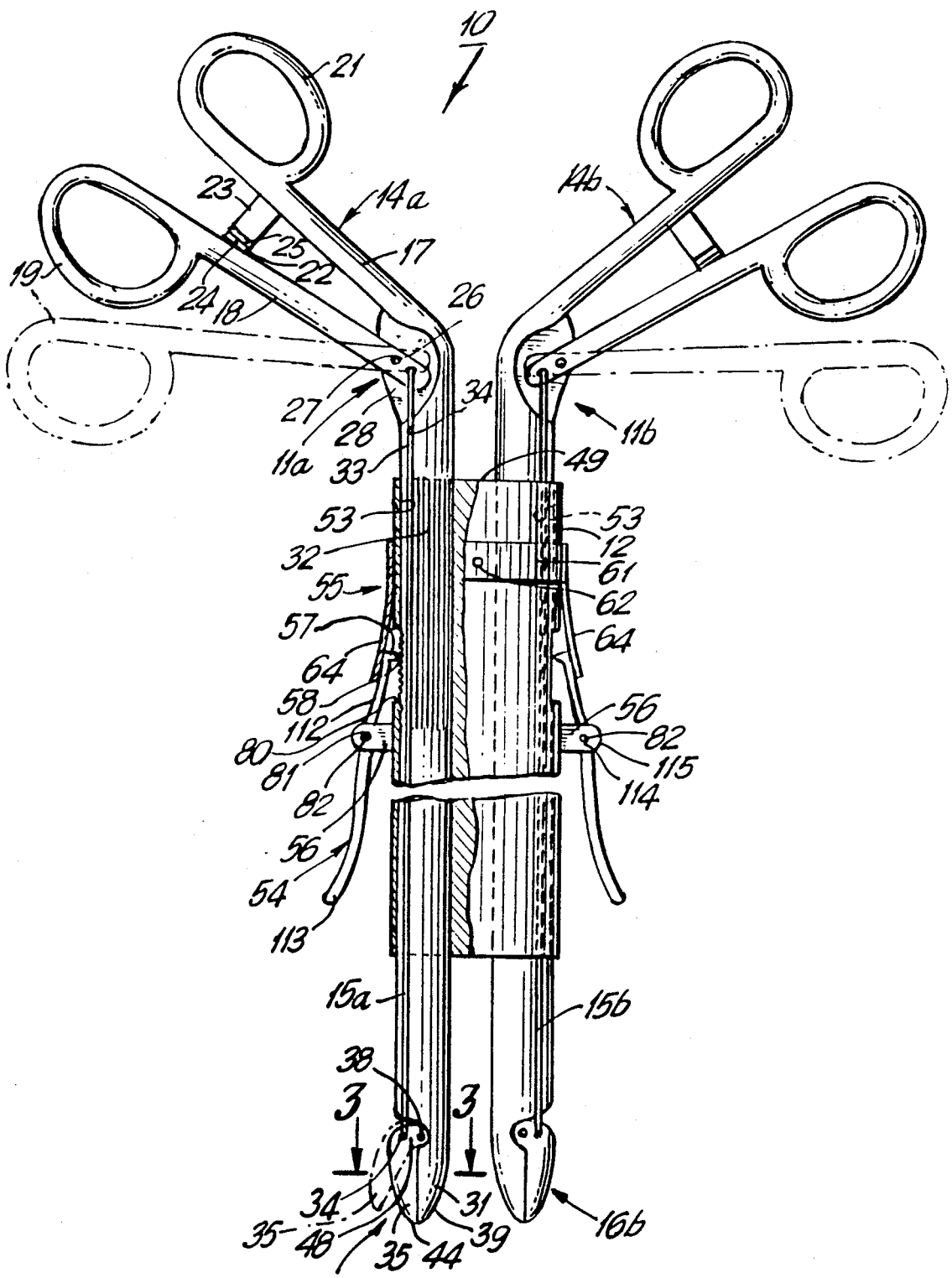
FIG. 1 is a view of the needle holder assembly, parts of which are cut away to illustrate the operation thereof.

As shown in FIG. 1, the endoscopic dual head curved needle holder 10 comprises two needle grasping and holding members 11a and 11b and a support cylinder 12 surrounding an intermediate portion of members 11a and 11b. The holding members 11a, 11b are similar in design and function and can be of the same or different dimensions in length, width or diameter. Their function is to hold a curved needle 13 (see FIG. 11) which may comprise a circular or eliptical arc. The needle 13 may be held simultaneously by both members 11a and 11b or separately by one of the members 11a, 11b allowing the transfer from one grasping surface to the other member's grasping surface.

Each needle grasping and holding member 11a, 11b includes a handle 14a, 14b, stem 15a, 15b and head 16a, 16b. Since the members 11a and 11b are similar, the description of member 11a will suffice. The handle 14a has two control ring limbs 17 and 18, approximately 9 cm. long, with 18 being movable with respect to the stem 15a and mounted thereto at a 45 degree angle. Limb 17 is a portion of and immovable with respect to member 18 and the stem 15. The limbs 17 and 18 terminate in rings 19, 21 which accommodate the operator's fingers.

In a preferred embodiment, the side of each limb 17 or 18 is between 2 mm and 10 mm wide and can be circular having a diameter between 2 mm and 10 mm in diameter. A typical ring 19, 21 is substantially eliptical, measuring 3 cm in its axial diameter and 2 cm in its diameter perpendicular to the limb axis. Each limb 17, 18 has a locking portion 22, 23 extending outwardly therefrom and facing one another with mating serrations 24, 25 which lock into position.

The movable limb 18 is coupled to the immovable limb 17 by a pin 26 which extends through recess 27 in the immovable limb 17. Limb 18 rotates about the pin 26 which is anchored in flange 28. A control wire 33 is mounted to one end of the limb 18 so that movement thereof about the pin 26 causes movement of the control wire 33 in a direction parallel to the stem 15a.

The stem 15a is a cylindrical rod 7 cm to 40 cm long, 5 to 25 mm in diameter and is attached to the handle 14a via the immovable (fixed) limb 17, and to the head 16a via the fixed jaw 31. At a distance of about 1 cm from the handle 14a, the stem 15a includes 0.5 to 1 mm deep longitudinal grooves 32, 0.5 to 1 mm apart circumferentially, which extend for a distance of 5 cm. These grooves 32 are parallel to each other and parallel to the long axis of the stem 15a. At a depth of 2 mm from the periphery and on the side of the handle 14a, there is a bore 34 running parallel to the long axis of the stem 15a which starts from the recessed flange 28 of the immovable limb 17 on the handle 14a and ends at the immovable jaw 31 of the head 16a. The control wire 33 is located within the bore 34 and is attached at its ends to the movable limb 18 of the handle 14a and the movable jaw 35 of the head 16a.

The head 16a (see FIG. 4-5) comprises a fixed jaw 31 and a movable jaw 35. At the proximal inside part of the fixed jaw 31, there is a recess 36 on each side forming a central ridge 29 along the main axis of the stem 15a with a bore 37 which accommodates a fixation pin or fulcrum 38 that secures the movable jaw 35 onto the immovable jaw 31, and allows the movable jaw 35 to rotate around its longitudinal axis. The jaws 31 and 35 are shown in open and closed positions in FIG. 1.

The immovable jaw 31 is fixed on the stem axis either as a direct extension of the stem 15a or as a separate component fixed to it by any conventional means. As shown in FIG. 4, the jaw 31 has a convex external surface 39 and a concave grasping surface 42. The grasping surface 42 is lined by horizontal curved grooves 43 (FIG. 4). This concave surface 42 would fit onto a cylinder of 3 mm to 100 cm radius, and is always the same as the radius of the convexity of the movable jaw 35 attached to the head 15a.

The movable jaw 35 and immovable jaw 31 each include a nose 44, body 46 and base 47, the nose 44 being located at the distal end and the base 47 located at the interior proximal end. As shown in FIG. 4, the movable jaw 35 has a recess 36 at its base between two horns 48. At the distal horns 48 and facing the end, there is a bore 36 which will line up with the bore 37 on the ridge of the immovable jaw 31 and together accommodate the pin 38 around which the movable jaw 35 will rotate. At the base of 47 and spaced from the surface away from the horns 48, there is a bore 34 to accommodate the control wire 33.

The cylinder 12, see FIG. 2, is a solid cylindrical rod of metal or plastic measuring from 5 mm to 15 mm in diameter and 3 cm to 40 cm in length. The cylinder 12 includes a head 51 and an elongated body 52. The controls are located in the head 51. The body part 52 is designed to enter through a port into the abdominal or other cavity of the human or animal body.

Starting from the flat surface 49 of the head 51 and ending at the flat surface of the body 52 are cylindrical bores 53 which can be of the same or of different diameter each to accommodate an endoscopic needle holder 11a, 11b of the same approximate diameter.

The head portion 51 is comprised of the supportive cylinder 12 and a rotational stop system. The rotation stop system permits or prevents the rotation of the needle holder 11a, 11b when in place at the command of the operator. The system includes a rotation stop 54, a ribbon spring 55 and a fulcrum tower 56. The rotation stop 54 comprises an irregular elongated member. The stop 54 includes a perpendicular extension 57 at one end to engage one or more indentations 58 of the same depth and width as the ridges-indentation (axial grooves) 32 of the stem 15a on the needle holder 11a. These grooves 58, when more than one, are arranged next to each other on a curve to engage the axial grooves 32 of the needle holder 11a. This curve is of the same diameter as the corresponding needle holder 11a which it is intended to engage.

The stop 54 (two may be employed) contacts the needle holder grooves 32 through a curved recess 80 at the periphery of the cylinder 12 of variable dimensions which expose the needle holder 11a and its axial groove 32 at the site of the head stop 54. The stop 54 is made of the proximal component 112 which is parallel to the main axis of the supportive cylinder and 1 mm away from the surface of the main cylinder 12. The body then curves away from the cylinder 12 to a distance of 1 cm from the main axis of the cylinder 12 and towards body of the cylinder 12 for a distance of 4 cm to form a release handle 113. Spaced from the flat component, is a bore 81 which will accommodate the fulcrum pin 82 around which the stop 54 can rotate. The body then curves further and is flattened out for a predetermined distance so that depression at this point 113 will disengage the perpendicular component of the stop from the needle holder.

The stop 54 is secured in place through the fulcrum fixation pin 82 which goes through the main body of the stop and through two bores 114 in the horns of the fulcrum tower 56. The fulcrum tower 56 has a body which is secured on the main support cylinder 12 and horns 115 at its opposite ends. The body of the stop 54 passes through the space between the horns and is secured with the fulcrum pin 82 which is secured inside the bores 81, 82 of the horns 115 and the stop 54.

The ribbon spring 55 comprises a peripheral ring 61 which is of 0.1 mm greater diameter than the support cylinder 12 and is secured on the support cylinder 12 with a fixation pin or screw 62 which goes through bores 63 of the peripheral ring 61 and corresponding site of the support cylinder 12 at a position 90 degrees away from the center of parallel limb of the rotation stop 54. The spring 55 also consists of two horns 64 or axial limbs which are of the same thickness as the peripheral ring and projecting towards the stem of the cylinder 12 and parallel to its main axis. The horns 64 are 90 degrees away from the fixation point of the peripheral ring 61 and they overlay the parallel limb of the rotation stop 54 for a predetermined distance securing the stop 54 gently on the particular needle holder groove 32 and preventing rotational motion of the needle holder 11a around its axis. This stop 54, however, allows free motion of the needle holder 10 parallel to the main axis of the cylinder 12 for a distance of 5 cm. Compression of the distal body of the rotation stop 54 disengages the stop 54 from the needle holder 11a and allows rotation of the needle holder 11a around its axis.

Figure 6:
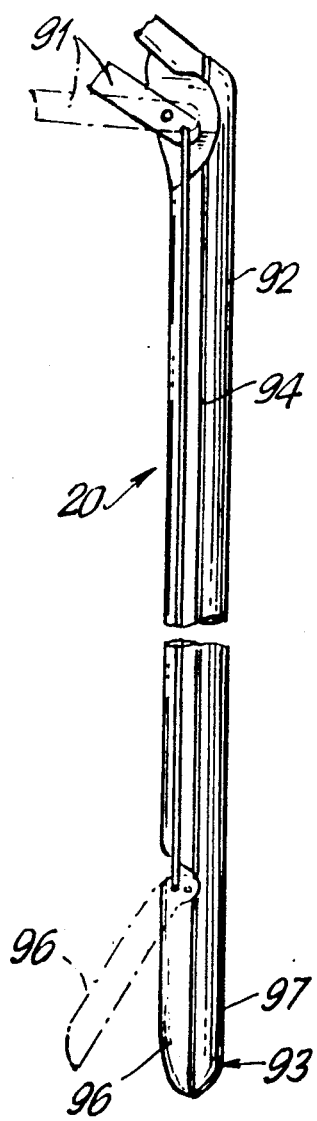
FIG. 6 is a view of the needle transporter with the movable jaw in phantom to illustrate the operation.
Figure 7:
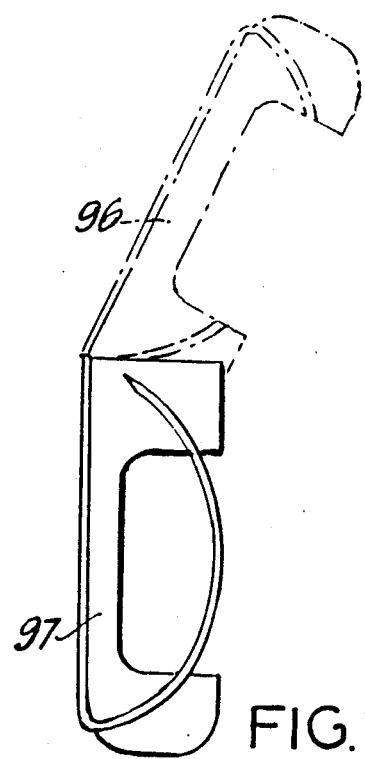
FIG. 7 is an enlarged view of the jaws of the needle transporter.
Figure 8:
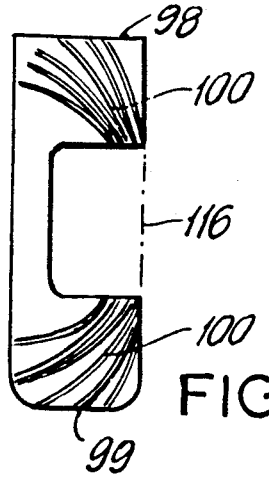
FIG. 8 shows the grooves on opposing surfaces of the jaws of FIG. 7 to accommodate needles

As shown in FIG. 6, the needle transporter 20 comprises a handle 91, a stem 92 and a head 93. The handle 91 and stem 92 are similar to the needle holder 11a in design with the following differences:

a) The handle 91 has a 1-2 mm groove (94) on the same line as the groove of the stem 92 as described below and is a direct extension of it to accommodate the tail of the thread 90;

b) The stem 92 does not have the axial grooves 32 that needle holder 11a and 11b have;

c) The stem 92 has one axial groove 94 that runs along a line on its surface 1-2 mm deep parallel to the main axis of the stem 92.

This groove 94 is a continuation of the groove at the side of the jaws of the transporter's head 93. The head 93 of the transporter 90 has two jaws 96, 97 which open and close in an identical fashion, like jaws 31 and 35 of the needle holder 11a. The jaws 96, 97 are of a different design as follows. Each jaw 96, 97 is of a shallow U-shape with one perpendicular limb 98 of the U being the base and the other perpendicular limb 99 the nose. The jaws 96, 97 in the entirety are of a rectangular shape with smooth edges at the distal end of the nose. The (opposing) grasping surface of each jaw 96, 97 is flat with corresponding grooves that oppose each other, leaving a 1 mm space between the jaws when fully closed. These grooves 100 comprise a part of the periphery of a circle whose center lies along a line starting at a point where it meets and bisects a line across the legs of the "U", extending towards the horizontal limb of the jaw passes through its center and continues to infinity. Line 116 is parallel to the main axis of the horizontal limb and joins the uppermost points of the grasping surface of the two perpendicular limbs. These grooves 100 extend to and through the periphery of the nose of each jaw and are 0.5 mm deep and 0.5 mm wide. The grooves 100 are part of the periphery of a circle with a radius at any point on line 116 and the line of every groove running through the point where line bisects line 116.

Figure 9:
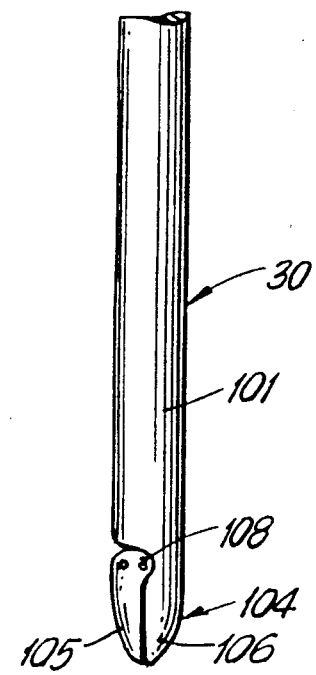
FIG. 9 is a partial view of the needle guide tissue forceps.
Figure 10:
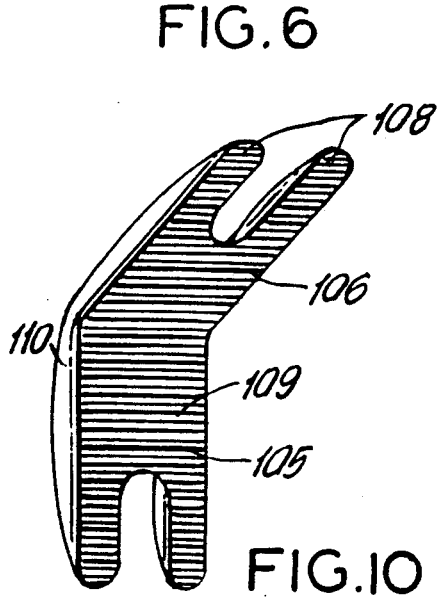
FIG. 10 is an enlarged detail of a portion of the jaws of the tissue forceps.

By closing the jaws 96, 97 of the transporter 20 over a needle 13 which lies along a groove 100, the needle 13 is secured in place with the point lying on the groove 100 of the proximal perpendicular limb and the tail at the distant perpendicular limb (nose) of the jaw, the thread continuing in the respective groove 94 and exiting at the nose. Along the periphery of the grasping surface of the jaws 96, 97 with the jaws 96, 97 closed and starting at the nose from the most distal point of line 116 and proceeding along the periphery of the nose towards and along the periphery of the base of the U, runs a 1 mm groove formed by the carved edges of the two jaws. This groove 100 extends along the same line on the stem of the instrument and (leads) communicates with all the curved grooves of the grasping surface of the jaws 96, 97. The purpose is to accommmodate the thread 90 of the needle The needle guide tissue forceps, as shown in FIG. 9, comprises a handle, a stem and a head similar to the holder 11a and are therefore not discussed in detail. The handle and the stem are identical to 10 except there are no peripheral grooves on the stem 103 of the forceps 101.

The head 104 has a movable 105 and an immovable jaw 106 that moves with exactly the same mechanism as needle holder 11a. Each jaw 105, 106 has a flat grasping surface 107 at its body and horns 108 with grooves 109 running at a right angle with the long axis of the instrument 1 mm apart. Each jaw 105, 106 has a body 110 and two horns 108. When the jaws 105, 106 are closed they hold the tissue in position so that the needle 13 can be passed into the tissue through the space between the horns 108; once the needle 13 is passed through the tissues, the jaws are opened and the tissue released.

As shown in FIG. 11, the endoscopic suture 40 comprises a needle (13) of a straight or curved configuration which is attached to a thread 90. The thread 90 ends with a terminal loop 41 which is formed either by knotting the end of a regular thread on itself or by manufacturing in continuum with the thread 90 without knotting. By passing the needle 13 through the tissue and then two to three times through the loop 41 a secure knot is formed and continous suturing can then follow in the conventional surgical fashion.

In operation, the components 11a, 11b and 12 are assembled into one instrument in a predetermined order and the components 11a and 11b are rotated so that they can both be in a position where they can both hold the curved needle 13 to be used for suturing, simultaneously with both heads locked. Once the desired position of the needle holders 11a and 11b is achieved, they are locked in place in relation to the support cylinder 12. The instrument is now ready to be used for endoscopic suturing using the chosen round (curved) needle 13.

The needle 13 is then released by both heads 16a, 16b, the heads locked and the instrument introduced through a port into the cavity where suturing is to take place. With both heads 16a, 16b pulled back towards the end of the cylinder 12, the chosen needle 13 is then introduced with the needle transporter 20 into the same cavity. Needle holder 11a (needle introducer) is then advanced one to three cm, the jaws 31, 35 opened and the needle 13 is moved close to the thread 90 between the jaws of the needle holder 11a and the jaws locked. The transporter jaws 93, 96 are then opened. The curved needle 13 is thus released to the needle holder 11a and the transporter 20 removed from the cavity via the port.

The tissue to be sutured is then grasped by needle guide tissue forceps 30 and the needle 13 inserted into and through the tissue at the space between the horns 108 of the needle guide tissue forceps. The needle holder 11b (needle extractor) is then advanced to the same level as holder 11a with its jaws open. The jaws of 11b are then closed securing the curved needle 13 towards its tip. Needle holder 11a then releases the curved needle 13 and is pulled back one to two centimeters. Needle holder 11b then pulls the needle 13 completely through the tissue and the thread 90 is pulled through the tissue to about 1 cm short of the terminal loop 41. Needle holder 11a is then advanced to the level as 11b, its jaws 31, 35 open, and it grasps the needle 13 at the same site where it was before. Needle holder 11b then releases the needle 13 and is withdrawn by 1-2 cm.

Needle holder 11a and needle holder 11b using the same steps introduces the needle 13 through the terminal loop 41 of the thread 90 two or three times and with another instrument, e.g., the tissue forceps 20. The thread 13 is pulled through the loop 41 all the way so that the loop 41 is secured on the tissues sutured with the tissues approximated. Continuous suture of the tissue. e.g., a bowel wall is continued by introducing the needle 13 with the needle holder 11a and extracting it with needle holder 11b as mentioned earlier. When the desired suture of the tissues is completed, the needle 13 is transfered to the needle transport instrument 20 by needle holder 11a, the thread 90 cut close to the needle 13 and the needle 13 removed from the abdominal cavity by the transporter 20. An instrument tie of the remaining thread 90 will then secure the suture line completing the work of this instrument's suture assembly.

While the invention has been explained by a detailed description of certain specific embodiments, it is understood that various modifications and substitutions can be made in any of them within the scope of the appended claims which are intended also to include equivalents of such embodiments.

What is claimed is:

1. An endoscopic suture assembly for insertion through a port within a body cavity and for suturing tissue in a laparascopic modality with a needle and suture thread comprises:
    a dual head curved needle holder, each needle holder including a handle at one end, an intermediate elongated stem and a head at the other end having a fixed jaw and a movable jaw for grasping a needle therebetween and a support cylinder extending about the stems;
    a needle transporter including a handle, an intermediate stem and a head having a fixed and a movable jaw for grasping and transporting a needle through a port into a body cavity and then releasing it after the needle has been grasped by the needle holder jaws;
    a needle guide tissue forceps comprising a handle, an elongated stem and a head including fixed and movable jaws for grasping and exposing between the jaws tissue to be sutured; and
    an endoscopic suture comprising a needle, a thread connected to one end thereof and a terminal loop at the other end of the thread to permit securing the suture without a conventional knot;
    wherein the needle is transferred from the transporter jaws to the needle holder jaws and moved back and forth between the jaws of the respective needle holders to suture tissue held by the needle guide tissue forceps.

2. An endoscopic suture assembly in accordance with claim 1 wherein:
    each needle holder includes a fixed limb and a movable limb, a control wire being connected to the movable limb at one end and to the movable jaw at the other end, said jaws being configured to grasp a needle therebetween at a fixed site of the needle and the stem of the needle holder includes a plurality of axial grooves along the upper surface thereof.

3. An endoscopic suture assembly in accordance with claim 2 wherein:
    the support cylinder comprises an elongated cylinder having apertures extending axially therethrough to accommodate the needle holder stems and a stop system comprising a ribbon spring having an upper ring portion mounted about the cylinder having an opening therethrough in the cylinder wall and downwardly extending legs, a fulcrum tower mounted to the cylinder body and extending outwardly therefrom and a stop member pivotably connected to the tower and engaging the axial grooves of the stem at one end to prevent rotation of the stem, said end being resiliently urged into engagement with the stem by the legs, which will allow the two needle holders to move at a constant relationship to each other and grasp the needle at a fixed site as desired.

4. A dual head needle holder comprising:
    a first and a second needle holder each comprising:
        a handle including a fixed limb and a movable limb
        an elongated stem having the movable limb pivotably connected thereto at one end and the fixed limb being mounted thereto at a predetermined angle at said end, and said stem having a a plurality of elongated grooves along the portion adjacent the limbs at the other end of the stem
        a head comprising a fixed jaw mounted to the stem and a movable jaw pivotably connected thereto, and a control wire mounted at one end to the movable limb and to the movable jaw at the other end for opening and closing said jaw with respect to the fixed jaw by movement of the movable limb.

5. A dual head needle holder in accordance with claim 4 wherein:
    the movable jaw includes a convex inner mating surface and the fixed jaw includes a concave inner mating surface, both of said inner surfaces having a plurality of grooves to grasp a needle therebetween in said grooves.

6. A dual head needle holder in accordance with claim 5 wherein:
    the fixed limb and the movable limb each include a loop at the other end thereof and means for locking said limbs together.

7. An endoscopic suture assembly in accordance with claim wherein:
    the needle transporter head comprises a pivotable jaw and a fixed jaw having a plurality of curved cooperating grooves therein to grip a curved needle and an elongated groove extending along the stem within which the suturing thread may be positioned.

8. An endoscopic suture assembly in accordance with claim 1 wherein:;
    the support cylinder includes means for locking one or both of the needle holders in a predetermined rotational position.

9. The method of performing endoscopic suturing within a body cavity comprising the steps of
    grasping tissue to be sutured with a forceps exposing the tissue between the jaws thereof;
    transporting a needle with suturing thread to the vicinity of the tissue;
    transferring the needle to a holding and grasping instrument having two heads and being positioned adjacent the exposed tissue;
    locking the heads to prevent rotation with respect to each other while permitting vertical movement;
    passing the needle from one head to the other head to perform suturing of the tissue; and
    transferring the needle to the transporting means to remove the needle from the body cavity.

10. The method of performing endoscopic suturing within a body cavity in accordance with claim 9 including the further steps of:
    passing the needle with the suturing thread attached thereto through a loop at the end of the thread to eliminate the ned for tying.

* * * * *